United States Patent [19]

Haase et al.

[11] 4,306,080

[45] Dec. 15, 1981

[54] PROCESS FOR THE PURIFICATION OF INDUSTRIAL EFFLUENTS

[75] Inventors: Jaroslav Haase, Basel; Peter Liechti, Arisdorf; Hans Wegmüller, Riehen; Rudolf F. Wurster, Pfeffingen; Quentin Bowes, Rheinfelden, all of Switzerland

[73] Assignee: Ciba-Geigy Corporation, Basel, Switzerland

[21] Appl. No.: 11,579

[22] Filed: Feb. 9, 1979

Related U.S. Application Data

[60] Division of Ser. No. 941,823, Sep. 11, 1978, Pat. No. 4,178,438, which is a continuation of Ser. No. 740,586, Nov. 10, 1976, abandoned.

[30] Foreign Application Priority Data

Nov. 14, 1975 [CH] Switzerland ............... 14798/75

[51] Int. Cl.³ ............... C07C 103/38; C07C 103/50
[52] U.S. Cl. ............... 564/197; 564/158; 564/160; 564/165; 260/465 D; 260/465.4
[58] Field of Search ......... 260/465 D, 465 A, 561 A, 260/557 R, 558 A; 564/197, 158, 160, 165

[56] References Cited

U.S. PATENT DOCUMENTS

| | | | |
|---|---|---|---|
| 2,277,015 | 3/1942 | Guest | 260/561 A X |
| 2,328,021 | 8/1943 | Katzman et al. | 260/561 A |
| 2,516,674 | 7/1950 | Bruce et al. | 260/561 A |
| 3,189,646 | 6/1965 | Rainer | 260/561 A |
| 3,978,125 | 8/1976 | Müller et al. | 260/561 A |

FOREIGN PATENT DOCUMENTS 2650999  5/1977  Fed. Rep. of Germany ... 260/561 A

OTHER PUBLICATIONS

Haase et al., CA 87:90395f (1977).
Haase et al., CA 87:69676p (1977).

*Primary Examiner*—Arthur P. Demers
*Attorney, Agent, or Firm*—Sprung, Felfe, Horn, Lynch & Kramer

[57] ABSTRACT

A novel process for the purification of industrial effluents, wherein the effluents are brought into contact with cationically modified, cellulose-containing materials, the cationic constituent of which is bonded to the cellulose part via the grouping of the general formula

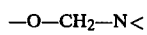

$$-O-CH_2-N<$$

in which the nitrogen belongs to an amide group of the cationic constituent and the oxygen is bonded to the cellulose part.

8 Claims, No Drawings

PROCESS FOR THE PURIFICATION OF INDUSTRIAL EFFLUENTS

This is a division of application Ser. No. 941,823 filed Sept. 11, 1978 (now U.S. Pat. No. 4,178,438) which is in turn a continuation of Ser. No. 740,586 filed Nov. 10, 1976 (now abandoned).

The present invention relates to a process for purifying industrial effluents, especially for decolorising effluents which are obtained in the textile, paper and leather industries and from the manufacture of dyestuffs and brighteners, such as, for example, filtrates, residual liquors, rinsing water and washing water. The process according to the invention is characterised in that the effluents are brought into contact with cationically modified, cellulose-containing materials in which the cationic constituent is bonded to the cellulose part via a grouping of the general formula

 (1)

in which the nitrogen belongs to an amide group of the cationic part and the oxygen is bonded to the cellulose part.

One of the great environmental problems in industrial regions is the pollution of rivers and lakes. Since the pollutants also come from industrial plants, the purification of industrial effluents is of increasing significance today. However, this effluent purification proves to be exceptionally difficult, especially when it concerns the elimination of organic substances which are dissolved in the water and are difficult to degrade biologically. Within the context of these problems there is, therefore, an urgent need for the decolorising and purification of effluents obtained in the dyestuffs, textile, paper and leather industries.

Various processes have already been proposed for the purification of deeply coloured and polluted effluents which are obtained, for example, from the manufacture and use of dyestuffs and textile or dyeing auxiliaries. Thus, for example, it is known to collect spent dyeing liquors or washing waters in large collecting tanks and to precipitate the dyestuff an auxiliary residues by adding suitable flocculating agents and to separate out the precipitate by sedimentation, flotation or filtration, which are frequently tedious. These processes have the disadvantage that the elimination of the resulting sludge is very expensive.

It has now been found, surprisingly, that a rapid and adequate purification of industrial effluents is achieved when these are brought into contact with cationically modified cellulose materials of the initially mentioned type. Compared with the known agents, for example activated carbon, these cellulose materials are distinguished by a high capacity for, and rate of, absorption of substances, especially anionic substances, which are dissolved or dispersed in water.

The new process is suitable, above all, for the purification of liquors which contain organic, ionic, that is to say anionic or cationic, substances or mixtures thereof. In particular, anionic or cationic dyestuffs, brighteners, dyeing auxiliaries or textile auxiliaries, surface-active agents, tanning agents and mixtures thereof can be removed from the effluents to a satisfactory extent. According to the invention, effluents which contain mixtures of anionic and/or cationic dyestuffs with anionic, cationic and/or non-ionic auxiliaries can be purified successfully. However, using the process according to the invention it is possible not only substantially to free incompletely exhausted dye liquors, brightening liquors and treatment liquors from the abovementioned substances, but also to purify the waste liquors which contain corresponding non-ionic textile auxiliaries or dyeing auxiliaries and/or non-ionic dyestuffs or brighteners and also liquors which are diluted by waste rinsing water and which usually contain mixtures of dyestuffs and washing agents, to a satisfactory extent.

By virtue of the great breadth of the field of application of the modified cellulose material it is possible to achieve a saving of fresh water by partial to complete recirculation of residual or waste liquors which are obtained; such a saving is demanded with ever increasing urgency today. Independently of the apparatus installed, the liquors concerned are, above all, the effluents obtained in connection with dyeing, washing and tanning processes in the dyestuffs, fibre, textile, paper and leather industries. In the case of a dyeing plant, for example, these effluents can originate from the customary dyeing apparatuses, such as those used for dyeing loose fibre material, tops, yarn and woven fabrics or knitted fabrics, and from cleaning equipment, for example from an open-width washing machine.

The purification of the effluents is appropriately carried out at 10° to 150° C. Preferably, however, it is carried out at between 20° and 100° C. and especially at between 30° and 70° C. If desired, the purification of the effluents can also be carried out under pressure or under vacuum. The pH value of the effluents can vary within wide limits, for example between 2 and 12. However, depending on the nature of the modified cellulose material used as the adsorbent, pH corrections, for example to a value of 2 to 9, and especially of 5 to 8, can facilitate and accelerate the purification process.

The process according to the invention can be carried out discontinuously, semi-continuously or continuously. In principle, the following embodiments are suitable in the sense of the invention: (a) the so-called stirring process in which the water to be purified is stirred with the cellulose material in a vessel or a series of vessels and then separated off; (b) the so-called fluidised bed process in which the cellulose material is kept in a suspended state by the flow of the liquor to be purified; and (c) the so-called fixed bed process in which the liquor to be purified is fed through cellulose material arranged in a filter-like manner.

If, of these three process variants, the fixed bed process (c) is used, suitable variants from the point of view of apparatus are, above all, the three which folllow:

1. The treatment apparatus, for example, the dyeing apparatus, is firmly connected to the adsorber installation.
2. The adsorber installation is movble and can be coupled with each treatment apparatus as required.
3. The effluents originating from the treatment liquors are combined in a suitable container and then fed together through the cellulose material.

Advantageous cationically modified cellulose materials are characterised in that their cationic constituent is bonded to the cellulose part via the grouping of the formula (2)

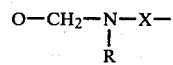 (2)

In this formula (2), X denotes the divalent bridge —CO—, —CO—O—, —CS—, >C=NH,

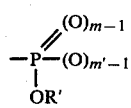

or —SO$_2$— or a carbon atom which is a constituent of a nitrogen heterocyclic structure and adjacent to the ring nitrogen. R and R' are hydrogen or an organic radical. m and m' in each case denote 1 or 2.

In formula (2), X above all denotes the —CO— bridge. R is preferably hydrogen or alkyl with 1 to 5 carbon atoms, which is optionally substituted by halogen, cyano, hydroxyl or alkoxy with 1 to 5 carbon atoms. The substituent R can also be a constituent of a nitrogen hetero-ring, in which the groupings —CO—, —CS— and >C=NH can also be included, as in derivatives of 5-pyrazolone, 5-aminopyrazole, barbituric acid or cyanuric acid. R can also optionally represent a further grouping —CH$_2$—O—(H), which is optionally also bonded to the cellulose. Amongst these radicals, R is appropriately —CH$_2$O(H) or preferably hydrogen. R' is preferably alkyl with 1 to 5 carbon atoms.

The cationic character of the modified cellulose materials which can be used according to the invention is due to the presence of basic substituents. The cellulose materials contain, as substituents of this type, which are bonded via the groupings of the formulae (1) and (2), for example amino groups, imino groups, quaternary ammonium or immonium groups, tertiary phosphino groups, quaternary phosphonium or sulphonium groups and also thiuronium or guanidium groups.

Preferred cationic substituents are amino groups, for example primary, secondary or, above all, tertiary amino groups, as well as quaternary ammonium groups. These contain, as N-substituents, aliphatic, cycloaliphatic or araliphatic groups and the N-substituents can also form 5-membered to 8-membered, and especially 6-membered, rings. The N-substituents are advantageously lower alkyl groups with, in each case, 1 to 5 carbon atoms, which are optionally substituted by hydroxyl or cyano groups.

Depending on the nature of the starting components used to manufacture the cationically modified cellulose materials, the cationic substituent can be bonded to the grouping of the formula (1) or (2) via any desired bridge members. Possible bridge members are, for example, divalent hydrocarbon radicals, for example lower, straight-chain or branched alkylene radicals, such as the methylene, 1,2-ethylene or 1,2- or 1,3-propylene group, the 1,4-cyclohexylene group or lower alkenylene radicals, such as the vinylene group, and also acid radicals which can be derived from an inorganic or organic polybasic acid, as well ureido, thioureido, guanidine or triazone groupings.

The methylolamide groupings and basic groupings required for the cationic modification of the cellulose materials can also be constituents of polymeric compounds, such as polycondensates, polymers or polyadducts.

Polymeric compounds of this type can correspond to the general formula $$T-B_d \qquad (3)$$

wherein T denotes a basic, polymeric parent substance, B denotes an amide grouping, especially a carboxylic acid amide group, and d denotes a number of at least 1, for example 1 to 200,000, and at least one amide group is methylolated and optionally also etherified. These polymeric compounds can be derived from homopolymers, copolymers, graft polymers or block polymers.

The basic groupings present in the parent substance T can be amino groups, such as, for example, primary, secondary or tertiary amino groups, and/or onium groups, such as, for example quaternary ammonium, sulphonium or phosphonium groups.

Cationic polymers containing methylol groups can be obtained, for example, by reacting basic, nitrogen-containing, polymeric compounds which contain groupings which can be methylolated, such as, for example, carboxylic acid amide groups, sulphonic acid amide groups, phosphonic amide groups or aminotriazine groups, with formaldehyde or formaldehyde donors, or also with glyoxal.

Suitable basic, nitrogen-containing, polymeric compounds in the abovementioned sense are, in principle, polymers which contain basic nitrogen atoms, which are capable of forming a salt, and amide groupings.

Suitable polymers are basic aminoplasts which are soluble in water or can be dispersed in water, such as, for example, formaldehyde-dicyandiamide condensation products. Appropriately, the reaction is carried out with condensation products of formaldehyde, dicyandiamide and one or more of the following components: urea, ammonium chloride and an alkylenepolyamine with, for example, a total of 2 to 18, and preferably with 2 to 8, carbon atoms and 2 to 5 amino groups.

The alkylenepolyamines are, for example, ethylenediamine, propylenediamine, butylenediamine, pentylenediamine, hexamethylenediamine, diethylenetriamine, triethylenetetramine, 1,2-propylenediamine, dipropylenetriamine, tripropylenetetramine, dihydroxydipropylenetriamine, dibutylenetriamine, tributylenetetramine, tetrabutylenepentamine, dipentylenetriamine, tripentylenetetramine, tetrapentylenepentamine, dihexamethylenetriamine, trihexamethylenetetramine and tetrahexamethylenepentamine.

Particularly suitable basic aminoplasts are, above all, formaldehyde-dicyandiamide, formaldehyde-dicyandiamide-ethylenediamine or formaldehyde-urea-dicyandiamide condensation products. Preferred products are obtained, for example, by a condensation reaction of formaldehyde, dicyandiamide and ammonium chloride or of formaldehyde with the reaction product of dicyandiamide and ethylenediamine or the corresponding acid salt, such as the hydrochloride, or ammonium chloride, and are described, for example, in Swiss Patent Specification 456,475, German Offenlegungsschrift No. 2,321,627 and French Pat. No. 2,189,327. Further basic aminoplasts are manufactured by a condensation reaction of urea, dicyandiamide and formaldehyde in the presence of an acid, such as hydrochloric acid, or by a condensation reaction of dicyandiamide with formaldehyde and the tetrahydrochloride of triethylenetetramine.

Reaction products, containing N-methylolamide groups, of halogenohydrins or dihalogenohydrins with alkylene- or polyalkylene-polyamines or -imines, such as, for example, reaction products of epichlorohydrin with diethylenetriamine, dipropylenetriamine or triethylenetetramine, or with polyethyleneimines, can likewise be employed as basic polymers. Basic reaction products of this type are described, for example, in German Auslegeschrift No. 1,010,736. Furtherbasic epoxide resins are epoxidised precondensates of aliphatic polyamines with polyepoxides, which are described, for example, in U.S. Pat. No. 3,346,519.

Basic polyamides which are manufactured by a condensation reaction of dibasic carboxylic acids containing 2 to 10 carbon atoms, for example adipic acid or its functional derivatives, such as, for example, esters, amides or anhydrides, with polyamines, especially polyalkylenepolyamines, such as those polyamides described, for example, in U.S. Pat. No. 2,882,185, are also suitable as basic, nitrogen-containing polymers.

The polyamidepolyamines which are obtained by reacting polymerised, preferably dimerised to trimerised, fatty acids with polyamines, appropriately in a ratio such that the polyamide resin formed has an amine value in the range of approximately 200 to 650 mg of potassium hydroxide per gram of polyamidepolyamine, are also of interest as basic polymers.

Basic polyamides which can be methylolated can also be condensation products of polymeric fatty acids with polyamines, such as those described in British Pat. No. 726,570 and No. 847,029 and it is possible to react these products with epoxide resins which are formed by reacting polyhydric phenols with polyfunctional halogenohydrins and/or glycerol dichlorohydrin and are described in U.S. Pat. No. 2,585,115 and No.2,589,245.

Further basic polyamide resins which can be methylolated are, for example, the products obtained by reacting halogenohydrins, for example epichlorohydrin, with aminopolyamides obtained from polyalkyleneamines and aliphatic dicarboxylic acids with 2 to 10 carbon atoms, such as the products described, for example, in U.S. Pat. No. 3,311,594.

Suitable polyamide resins which can be used to manufacture the cationically modified cellulose materials are also described, for example, in British Pat. Nos. 726,570, 810,348, 811,797, 847,028, 865,656 and 1,108,558.

Basic polyamides obtained from a reaction mixture which contains polymeric fatty acids (manufactured in accordance with British Pat. No. 878,985 and No. 841,544), monomeric fatty acids and lower polyalkylenepolyamines by condensation polymerisation at high temperatures can also be used for the manufacture of the cationically modified cellulose materials.

Further basic polymers are the polymers of an alkyleneimine with 2 to 4 carbon atoms which have an average molecular weight (MW) of 500 to 200,000, and preferably 10,000 to 40,000, and contain at least one methylolamide group. These polymers as a rule possess a Brookfield viscosity at 20° C. of 500 to 20,000 centipoise (cp). Suitable alkyleneimines are, in particular, ethyleneimine, propyleneimine, 1,2-butyleneimine and 2,3-butyleneimine. Of all the alkyleneimines, ethyleneimine is preferably used. The methylolamide group can be introduced, for example, by reacting the polyalkyleneimine with chloroacetamide and subsequently methylolating the reaction product.

Cationic polymers containing 2-vinyl-1-cycloamidinepropionamide groupings which have been methylolated or glycolated with glyoxal are also advantageous polymers which can be employed to modify the cellulose. Such polymers are described, for example, in U.S. Pat. No. 3,772,259.

N-Methylolamide group-containing addition polymers and copolymers, such as, for example, optionally quaternised copolymers of base-substituted maleimides, acrylic acid esters and acrylamides as well as vinylpyridine and ethylenically unsaturated comonomers are also suitable as basic polymers. Examples of suitable comonomers which may be mentioned are: alkyl acrylates or methacrylates with 1 to 12 carbon atoms in the alkyl radical, which can optionally also be further substituted, especially by hydroxyl groups, such as methyl acrylate or methacrylate, ethyl acrylate or methacrylate, β-hydroxyethyl acrylate or methacrylate, n-butyl acrylate or methacrylate and dodecyl acrylate or methacrylate; (meth)-acrylic acid, (meth)-acrylamide and (meth)-acrylonitrile; vinyl esters of aliphatic carboxylic acids containing 1 to 12 carbon atoms, or mixtures of such carboxylic acids, such as vinyl acetate, vinyl formate and vinyl butyrate or vinyl esters of a mixture of carboxylic acids with 9 to 11 carbon atoms; vinylbenzenes, such as styrene, chlorostyrene and methyl-styrene; and maleic acid monoalkyl esters and monoalkylamides.

N-Methylolamide group-containing polymeric reaction products of α,ω-dihalogenoalkanes or bis-chloromethyl-aromatic compounds with amino compounds, such as, for example, dialkylamines or peralkylated polyamines, especially diamines, are also suitable.

Moreover, basic polymers which contain N-methylolated urea, urethane, amidine or guanidine groupings can be employed to modify the cellulose materials.

Acyclic and cyclic monoamines or polyamines, monoimines or polyimines, or quaternary ammonium salts of these amines and imines, each of which contain at least one N-methylolamide group, are advantageously suitable for the cationic modification of the cellulose materials. The methylolamide group is capable of reacting with the hydroxyl groups in the cellulose, so that the basic compound is bonded to the cellulose part via the grouping of the formula (1) or (2).

It is particularly advantageous when the cellulose materials are cationically modified with an amino compound which contains at least one amino group and at least N-methylolamide group, especially a N-methylolcarboxamide group, which is optionally etherified by $C_1$–$C_4$-alkoxy. Amino compounds of this type can advantageously be derived from aliphatic monoamines or polyamines or from hydrogenated nitrogen-heterocyclic compounds, for example pyrrolidine, piperidine, pipecolines, morpholine or piperazines, but especially from a monoamino compound which contains a single methylolamide group.

Monoamino compounds containing an optionally etherified N-methylolcarboxamide group which are particularly suitable according to the invention are the compounds of the general formula

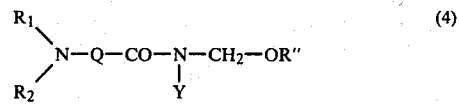

(4)

in which R" denotes $C_1$–$C_4$-alkyl or, preferably, hydrogen, $R_1$ and $R_2$ independently of one another denote hydrogen, lower alkyl which is optionally substituted by halogen, hydroxyl, lower alkoxy or cyano, or cycloalkyl, benzyl or the group of the formula $$-Q-CO-\underset{Y}{N}-CH_2-OR'' \quad (5)$$

or $R_1$ and $R_2$, together with the nitrogen atoms which links them, denote a 5-membered or 6-membered heterocyclic radical, such as, for example, pyrrolidinyl, piperidino, morpholino or piperazinyl, Q denotes an alkylene- or alkyl-substituted alkylene chain with up to 8 carbon atoms, preferably $C_1$–$C_3$-alkylene, and Y denotes hydrogen, lower alkyl or —$CH_2OR''$. Methylol compounds of the formula (4) which contain only a single grouping of the formula (5) are particularly preferred. In these methylol compounds, $R_1$ and $R_2$ are appropriately both lower alkyl or lower alkoxy-lower alkyl or form, together with the common nitrogen atom, a morpholino radical. $R_1$ and $R_2$ are, however, preferably lower alkyl, Y is preferably hydrogen and $R''$ is especially hydrogen.

Such methylol compounds of the formula (4) can be obtained by reacting an amino compound with an amide of a 1,2-unsaturated, aliphatic carboxylic acid or with a halogenoacetamide and methylolating the reaction product with formaldehyde or a formaldehyde donor, such as, for example, paraformaldehyde or trioxane. Suitable monoamines are, in particular, monoalkylamines or dialkylamines with 1 to 4 carbon atoms in each alkyl radical or optionally alkoxylated $C_2$–$C_4$-alkanolamines with 1 to 4 carbon atoms in any alkoxy radical which may be present and suitable amides are acrylamide, maleic acid diamide or chloracetamide.

Preferred cationically modified cellulose materials can be obtained when the modification is carried out with polyamino compounds which contain at least one N-methylolcarboxamide group and which are derived, for example, from alkylenepolyamines or hydrogenated diazines, especially from a N,N-dialkyl-ethylenediamine or a N,N-dialkyl-propylenediamine or piperazine. Polyamino compounds of the general formula

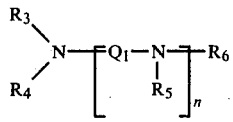 (6)

in which $Q_1$ denotes an alkylene- or alkyl-substituted alkylene chain with up to 8 carbon atoms, preferably $C_2$–$C_3$-alkylene, $R_3$, $R_4$, $R_5$ and $R_6$ independently of one another denote hydrogen, lower alkyl which is optionally substituted by hydroxyl, cyano, halogen or lower alkoxy, or cycloalkyl, benzyl or the group of the formula (5), or $R_3$ and $R_4$, together with the nitrogen atom which links them, denote a 5-membered or 6-membered heterocyclic radical, for example of the type mentioned above for $R_1$ and $R_2$, or, if n is 1, $R_4$ and $R_5$, together with the grouping $>N-Q_1-N<$ which links them, also denote a divalent heterocyclic radical, especially a piperazino ring, and n denotes 1 to 1,000, preferably 1 to 4 and especially 1, and at least one of $R_3$, $R_4$, $R_5$ and $R_6$ represents the group of the formula (5) and, if n denotes more than 1, each $R_5$, independently of the others, can represent hydrogen, lower alkyl which is optionally substituted by hydroxyl, cyano, halogen or lower alkoxy, or cycloalkyl, benzyl or the group of the formula (5), or each $R_5$, or individual $R_5$s, together with the adjacent $R_5$ and with the grouping $>N-Q_1-N<$ which links them, can also represent a divalent heterocyclic radical, especially a piperazino ring, are especially suitable.

Amongst the polyamino compounds of the formula (6), those wherein n is 1 and which correspond to the diamino compounds given below, of the formula

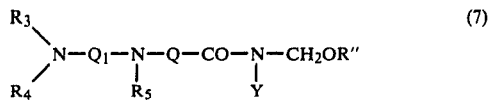 (7)

wherein $R_3$, $R_4$, $R_5$, $R''$, Q, $Q_1$ and Y have the indicated meaning, are preferred.

Diamino compounds of the formula (7) in which $R_3$ and $R_4$ both denote lower alkyl and $R_5$ denotes the group of the formula (5), or $R_4$ and $R_5$, together with the grouping $>N-Q_1-N<$ which links them, denote a piperazino ring and $R_3$ denotes the group of the formula (5), Q denotes $C_1$–$C_3$-alkylene, $Q_1$ denotes ethylene or propylene and Y denotes hydrogen, are particularly preferred.

Methylolamide compounds which contain at least one onium group, especially a quaternary ammonium group, are of particular practical interest for modification of the cellulose materials. Advantageously, ammonium salts of this type correspond to the following formulae (8), (9) and (10):

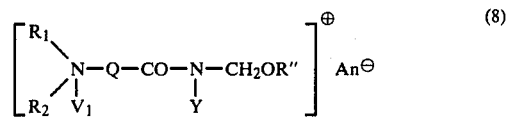 (8)

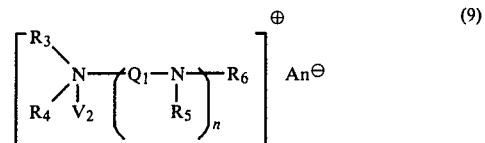 (9)

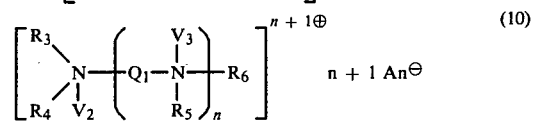 (10)

wherein $V_1$, $V_2$ and $V_3$ independently of one another denote hydrogen, lower alkyl which is optionally substituted by halogen, cyano, hydroxyl or lower alkoxy, or benzyl or the group of the formula (5), $R_1$, $R_2$ and $V_1$, or $R_3$, $R_4$ and $V_2$, together with the nitrogen atom which links them, denote a pyridine ring which is optionally substituted by lower alkyl and $An^\ominus$ denotes the anion of an organic or inorganic acid, and $R_1$, $R_2$, $R_3$, $R_4$, $R_5$, $R_6$, $R''$, Q, $Q_1$, Y and n have the meaning indicated for formulae (6) and (7) and at least one of $R_3$, $R_4$, $R_5$, $R_6$, $V_2$ and $V_3$ represents the group of the formula (5) and, if n denotes more than 1, each $R_5$ or each $V_3$, independently of the others, can represent hydrogen, lower alkyl which is optionally substituted by halogen, cyano, hydroxyl or lower alkoxy, or benzyl or the group of the formula (5), or each $R_5$, or individual $R_5$s, together with the adjacent $R_5$ and with the common grouping $>N-Q_1-N<$, can also represent a divalent heterocyclic radical, especially a piperazino ring. The compounds of the formula (10) can also be only partially quaternised with $V_3$ in the recurring units of the formula

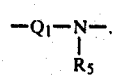

Amongst the quaternary ammonium compounds of the formulae (8), (9) and (10), the quaternary ammonium salts of the formula (11)

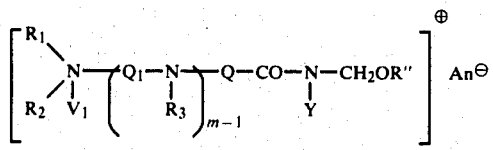

in which $R_1$, $R_2$, $R_3$, $R''$, $V_1$, $Q$, $Q_1$, $Y$, $An^\ominus$ and $m$ have the indicated meaning, are preferred.

Ammonium salts of the formula

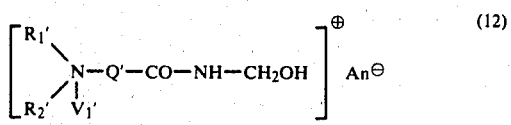

or of the formula

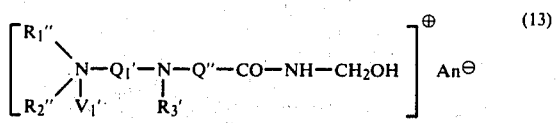

wherein $R_1'$, $R_2'$, $V_1'$, $R_1''$ and $R_2''$ each denote lower alkyl, or $R_1'$ and $R_2'$, together with the nitrogen atom which links them, denote a morpholino ring, $R_3'$ denotes hydrogen or the group of the formula —Q'—CO—NH—CH$_2$OH, $Q'$ denotes methylene or propylene, $Q_1'$ denotes ethylene or propylene, $Q''$ denotes $C_1$–$C_3$-alkylene and $An^\ominus$ has the indicated meaning, are particularly preferred.

Quaternised polymeric compounds of the formula (14) or block copolymers of the formula (15)

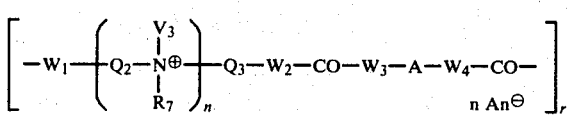

or

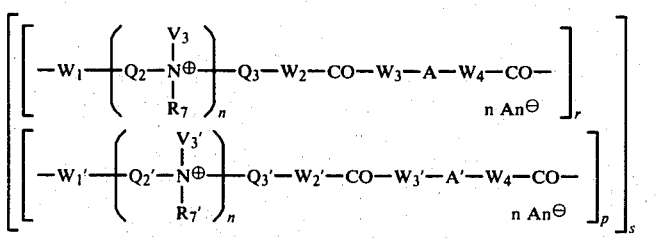

which can also be only partially quaternised, can also be employed to modify the cellulose materials.

In the formulae (14) and (15), $Q_2$, $Q_3$, $Q_2'$ and $Q_3'$ independently of one another denote an alkylene- or alkyl-substituted alkylene chain with 2 to 8 carbon atoms, and preferably with 2 to 4 carbon atoms, $V_3$, $R_7$, $V_3'$ and $R_7'$ independently of one another denote hydrogen, lower alkyl which is optionally substituted by halogen, hydroxyl, cyano or lower alkoxy, or benzyl or the group of the formula (5a)

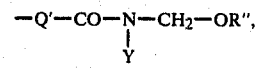

$Q'$ denotes methylene or propylene, $W_1$, $W_2$, $W_1'$ and $W_2'$ independently of one another each denote a direct bond, oxygen or the group >N—Y; $W_3$, $W_4$, $W_3'$ and $W_4'$ each denote a direct bond or —NH—; —CO—A—CO— and —CO—A'—CO— each denote the radical of a polybasic carboxylic acid, especially the radical of a saturated or unsaturated aliphatic dicarboxylic acid, or the radical of an aromatic dicarboxylic acid, such as of terephthalic acid or isophthalic acid or of naphthalene-2,6-dicarboxylic acid, $r$ and $p$ each denote 1 to 10,000 and $s$ denotes 1 to 10 and $n$, $An^\ominus$, $R''$ and $Y$ have the indicated meaning and at least one of $V_3$, $R_7$, $V_3'$, $R_7'$ and $Y$ represents the group of the formula (5a) and, if $n$ is more than 1, each $R_7$ or $V_3$ and each $R_7'$ or $V_3'$, independently of the others, can represent hydrogen, lower alkyl which is optionally substituted by halogen, cyano, hydroxyl or lower alkoxy, or benzyl or the group of the formula (5a), or each $R_7$ and $R_7'$ or individual $R_7$s and $R_7'$s, together with an adjacent $R_7$ or $R_7'$ respectively and with the grouping >N—Q$_2$—N< and >N—Q$_2'$—N< which link them, can represent a divalent heterocyclic radical, especially a piperazino ring.

Amongst the quaternised polymeric compounds of the formula (14), those which correspond to the formula (16)

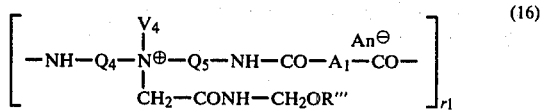

wherein $Q_4$ and $Q_5$ each denote $C_2$–$C_4$-alkylene, $R'''$ denotes hydrogen or methyl, $V_4$ denotes lower alkyl and $A_1$ denotes the radical of an aliphatic $C_2$–$C_4$-dicarboxylic acid, especially $C_2$–$C_4$-alkylene, and $r_1$ denotes 2 to 100 and $An^\ominus$ has the indicated meaning, are particularly preferred.

Addition polymers and copolymers such as, for example, optionally quaternised polymers of N-substituted maleamides or maleimides or copolymers of N-substituted maleimides and ethylenically unsaturated monomers, for example styrene, are also suitable as basic polymers for the cationic modification of the cellulose materials. Polymers and copolymers of this type have, in the molecule, for example, recurring units of the formulae (17) and (18)

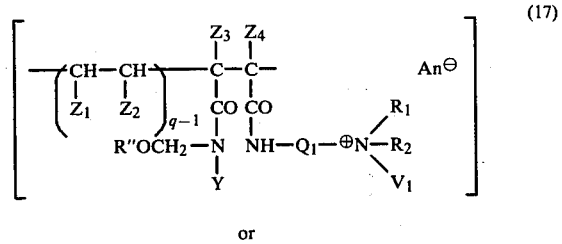

or

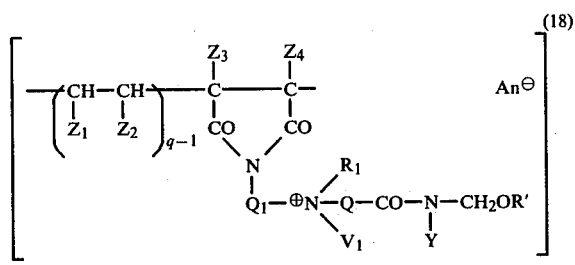

in which one of $Z_1$ and $Z_2$ denotes hydrogen and the other denotes hydrogen, lower alkyl, cyano, carboxyl or carbamoyl, $Z_3$ and $Z_4$ independently of one another denote hydrogen or lower alkyl and q denotes 1 or, preferably 2, and $R_1$, $R_2$, R'', $V_1$, Q, $Q_1$, Y and $An^\ominus$ have the indicated meaning.

Advantageous other polymers of ethylenically unsaturated monomers have recurring units of the formulae (19) and (20)

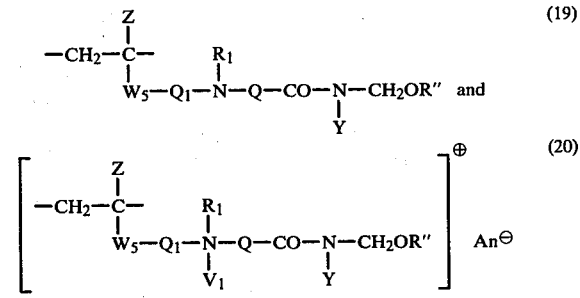

wherein $W_5$ denotes oxygen, —COO— or

and Z and Z' each denote hydrogen or lower alkyl, such as, for example, methyl, and Q, $Q_1$, $R_1$, R'', $V_1$, Y and $An^\theta$ have the indicated meaning.

These recurring units of the formula (19) and (20) can also be incorporated in copolymers with other copolymerisable vinyl compounds, for example the above-mentioned ethylenically unsaturated comonomers.

In the definition of the radicals of the compounds of the formulae (4) to (16), which can be used to modify the cellulose materials, and of the recurring units of the formulae (17) to (20), lower alkyl and lower alkoxy as a rule represent those groups which contain 1 to 5, and especially 1 to 3, carbon atoms, such as, for example, methyl, ethyl, n-propyl, isopropyl, n-butyl, sec.-butyl or amyl, or methoxy, ethoxy or isopropoxy. Halogen, in connection with all of the above substituents, denotes, for example, fluorine, bromine or, preferably, chlorine.

The cationic modification is as a rule effected by treating, for example, impregnating, the cellulose materials with the cationic methylol compound, or mixtures which form it, in an acid medium, for example at a pH value of 2 to 6, and heat-setting the treated cellulose materials, appropriately at temperatures of between 20° and 200° C., and preferably between 50° and 150° C., heat-setting being carried out until the product is dry. Mixtures of the basic methylol compounds can also be employed to modify the cellulose. A catalyst can optionally be used for setting. Suitable catalysts, are, for example, ammonium thiocyanate, ammonium chloride, ammonium hydrogen orthophosphate, magnesium chloride, zinc nitrate, maleic acid, tartaric acid or citric acid.

The cationic methylol compounds can also be etherified with an alkanol containing at most 4 carbon atoms, for example with ethanol, propanol, butanol or, especially, methanol.

The resulting cationically modified cellulose materials as a rule contain at least 0.4% by weight, and preferably 0.7 to 1.5% by weight, of basic nitrogen. The total nitrogen content, which also includes the amide nitrogen, is as a rule at least 0.6% by weight and preferably 0.8 to 3% by weight.

Aminoplast precondensates which do not contain any basic groups, such as, for example, primary, secondary or tertiary amino groups or quaternary ammonium groups, can optionally also be used as reactants. Aminoplast precondensates are understood as addition products of formaldehyde and methylolated nitrogen compounds, such as, for example, urea compounds or thiourea compounds or 1,3,5-aminotriazines.

Suitable urea compounds and thiourea compounds are, for example, urea, thiourea, substituted ureas, such as alkylor aryl-ureas, alkyleneureas and alkylenediureas, such as ethyleneurea, propyleneurea, dihydroxyethyleneurea, hydroxypropyleneurea and acetylenediurea, and also dicyandiamide, dicyandiamidine, urones and hexahydropyrimidones.

Examples of 1,3,5-aminotriazines which may be mentioned are: melamine and N-substituted melamines, such as N-butylmelamine, N-trihalogenomethylmelamines, triazones, ammeline, guanamines, such as, for example, benzoguanamine, acetoguanamines and diguanamines, as well as guanidines which can be brought into a water-soluble form by conversion into corresponding ammonium salts.

Aminoplast precondensates which can be used are, preferably, the methylol compounds of the said ureas and 1,3,5-aminotriazines. Amongst these compounds, those to be singled out in particular are, above all, N-methylolureas and N-methylolmelamines. Partial ethers of such methylol compounds, for example with alkanols with 1 to 4 carbon atoms, such as methanol, ethanol, n-propanol or n-butanol, can also be used.

The cellulose-containing materials to be used for cationic modification are bleached or unbleached pine sulphite cellulose, kraft sulphate cellulose, paper, cardboard products, textile fibres made of cotton, rayon staple, jute, ramie, hemp, linen or viscose and also peat, mechanical wood pulp, sawdust, wood fibres, wood flour, cork flour, bark or cereal waste. Waste paper, the use of which is usually associated with problems, can also be employed. These cellulose materials are appropriately converted into a form suitable for treatment with the methylol compound, for example into a fibre suspension. The cellulose can also be in the form of granules, filter paper, absorbent paper or paper pulp.

If desired, the cationically modified cellulose material to be used according to the invention can be mixed with activated carbon and/or other known filtration aids, such as, for example, peat, kieselguhr or diatomaceous earth. In this case, for example, the activated carbon is added to the cellulose materials in amounts of 2 to 95% by weight, and preferably of 10 to 70% by weight, calculated relative to the total weight of the cellulose material.

Anionic or cationic dyestuffs or optical brighteners which are water-soluble or disperse in water are possible as dyestuffs which are removed, according to the invention, from the effluents. The process according to the invention is preferably suitable for removing water-soluble, and especially anionic, dyestuffs or optical brighteners.

The anionic dyestuffs are dyestuffs in which the anionic character is due to the formation of a metal complex alone and/or to acid substituents conferring solubility in water. Possible acid substituents of this type, which confer solubility in water, are carboxylic acid groups, phosphoric acid groups, acylated sulphonimide groups, such as alkyl- or aryl-disulphimide groups or alkyl- or aryl-carbonylsulphimide groups, or alkyl- or aryl-imide groups, sulphuric acid ester groups and, above all, sulphonic acid groups.

The anionic dyestuffs can belong to very diverse categories of dyestuffs. Examples which may be mentioned are oxazine, triphenylmethane, xanthene, nitro, acridone, stilbene, perinone, naphthoquinone-imine, phthalocyanine, anthraquinone and azo dyestuffs. The latter can be metal-free, metallisable or metal-containing monoazo, disazo and polyazo dyestuffs, including the formazane dyestuffs, wherein the metal atom forms a 1:1-complex or 1:2-complex, especially 1:2-chromium or 1:2-cobalt complexes, which contain two identical or two different molecules of azo dyestuff bonded as a complex to a chromium or cobalt atom. These dyestuffs can also contain, in the molecule, so-called reactive groupings which enter into a covalent bond with the fibre material to be dyed.

The cationic dyestuffs which can be removed from the effluents with the aid of the cellulose material are, quite generally, the customary salts and metal halide double salts, for example zinc chloride double salts, of the known cationic dyestuffs in which the cationic character emanates from a carbonium, oxonium or sulphonium group and above all from an ammonium group. Examples of such chromophoric systems are: methine, azomethine, azo, hydrazone, azine, oxazine, thiazine, diazine, xanthene, acridine and polyarylmethane, such as diphenylmethane or triphenylmethane, dyestuffs as well as coumarin and azo dyestuffs which contain an indolinium, pyrazolium, triazolium, tetrazolium, oxadiazolium, thiodiazolium, oxazolium, thiazolium, pyridinium, pyrimidinium or pyrazinium ring. They can also be arylazo, phthalocyanine and anthraquinone dyestuffs which carry an external ammonium group, for example an external cyclammonium or alkylammonium group.

The modified cellulose material is not only suitable for decolorising residual liquors obtained from the manufacture of dyestuffs and from textile dyeing, paper dyeing and leather dyeing but in addition also renders good service when the problem is to remove residues of anionic or cationic optical brighteners from washing liquors and bleaching liquors. Particularly advantageous results are obtained in those cases in which the optical brightener to be eliminated is of anionic character.

The optical brighteners can belong to any category of brighteners. The anionic brighteners are, in particular, stilbene compounds, pyrazolines, dibenzoxazolyl or dibenzimidazolyl compounds or naphthalic acid imides which contain, in the molecule, at least one acid group, such as a carboxylic acid group or, preferably, a sulphonic acid group and can be fibre-reactive. In the case of the cationic brighteners, these are, above all, optical brighteners of the methine, azamethine, benzofurane, benzimidazolyl, coumarin, naphthalimide or pyrazoline series.

A further advantage of the modified cellulose material is based on the fact that it enables non-ionic, anionic and cationic surface-active agents and textile and dyeing auxiliaries, as well as phosphates, also to be eliminated, at least partially, in addition to the dyestuffs, from aqueous residual liquors. Such auxiliaries are described in more detail in the book "Tenside-Textilhilfsmittel-Waschrohstoffe" ("Surfaceactive agents—textile auxiliaries—detergent raw materials") by Dr. Kurt Lindner (published by Wissenschaftlicher Verlagsgesellschaft Stuttgart 1964). Anionic compounds of the alkylarylsulphonic acid type are of particular interest in practice.

The modified cellulose material can also be of assistance where the problem is the elimination of anionic synthetic tanning substances, especially tanning substances which carry one or more sulpho groups in the molecule. A more detailed description of these compounds is given in, for example, "Ullmans Encyklopädee der technischen Chemie" ("Ullmann's Encyclopaedia of Industrial Chemistry"), volume 11, pages 595–598. The cationically modified cellulose material also serves as a general anion exchanger.

By suitable choice of the cellulose material it is possible, according to the invention, to remove up to 100% of the dissolved impurities from the effluents. Retention effects of up to 50 g of residual substance, that is to say dyestuff, optical brightener, auxiliary, washing agent or tanning substance, per 100 g of cellulose material can be achieved. In cases in which it is not possible to achieve complete decolorising or removal of the residual substances by a single treatment of the residual liquor with the cellulose material, it is advisable to repeat the purification process.

After the impurities have been adsorbed, the charged cellulose materials can easily be regenerated with the aid of, for example, a dilute aqueous solution of sodium hydroxide.

An advantage of the process according to the invention which is particularly economical is that the cationically modified cellulose materials used can, after they have been saturated with the residual substances from the effluents, be dehydrated in a simple manner, dried and then fed to a combustion process or can be used as additives, for example for the manufacture of packing and building materials. A further advantage may be seen in the fact that the cationically modified cellulose materials can be converted into the desired use forms, such as, for example, fibres, chips and filter paper, in a simple manner.

The cationically modified cellulose materials can advantageously be employed in effluent purification in place of flocculating agents, there being no problems of overdosage. Because of the good drainage properties, sludge problems are also avoided. Furthermore, the cationically modified cellulose materials are distinguished by a high retention of anionic substances in a neutral pH range. In particular, the high throughput capacity when the cationically modified cellulose materials are used in a suitable form, such as, for example, chips, in the fixed bed process is of great significance.

In the manufacturing instructions and examples which follows, percentages are always percentages by weight.

MANUFACTURING INSTRUCTIONS

A.

(a) 115 g of an adduct obtained by an addition reaction of 2 mols of acrylamide with 1 mol of N,N-dimethylethylenediamine are dissolved in 93 ml of water and the solution is allowed to react, at a temperature of 0°–10° C., with 85 ml of a 35.1% strength solution of formaldehyde until the content of free formaldehyde is 0.7%. 293 g of a 50% strength aqueous solution of the dimethylol compound of the formula $$(CH_3)_2N-CH_2-CH_2-N(CH_2CH_2-CONH-CH_2OH)_2 \quad (101)$$

are obtained.

The solution is then diluted with 1,172 g of water and the pH is adjusted to 3 with concentrated hydrochloric acid.

(b) 9.1 g of filter paper (weight per unit area 100 g/m$^2$) are so saturated with the acid solution prepared according to a) that 25.7 g of the acid solution are taken up by the paper. The impregnated paper is dried for 10 minutes at 105°–110° C., and then suspended in 1 liter of water with the aid of a high speed stirrer. The paper slurry is then filtered and the material on the filter is washed with distilled water and dried in vacuo. The total nitrogen content of this fibre-like adsorbent is 2.15%, 1.07% of which is basic nitrogen. Similarly good adsorbents are obtained when sulphite cellulose pulp, cotton yarn or cotton fabric is employed in Instruction A. (b) in place of the filter paper and in an equal amount.

B.

(a) 43.2 g of an adduct obtained by an addition reaction of 1 mol of diethylamine with 1 mol of acrylamide are dissolved in 35.4 g of water and methylolated with 25.8 g of a 35% strength formaldehyde solution, with the addition of 0.1 g of sodium hydroxide, for 5 hours at 50°–60° C. A 50% strength, yellowish solution of a methylol compound of the formula $$(C_2H_5)_2N-CH_2CH_2-CONH-CH_2OH \quad (102)$$

which contains 0.77% of free formaldehyde is obtained.

This solution is then diluted with 417.5 g of water and the pH is adjusted to 3 with concentrated hydrochloric acid.

(b) 9.5 g of filter paper are so saturated with the acid solution prepared according to (a) that 30.4 g of the acid solution are taken up by the paper. The impregnated paper is dried for 10 minutes at 110° C. and then worked up as described in Instruction (A.b). The total nitrogen content of this adsorbent is 2.07%, 1.03% of which is basic nitrogen.

C.

(a) 63.2 g of an adduct obtained by an addition reaction of acrylamide with morpholine are introduced into a suspension of 18 g of paraformaldehyde and 0.2 g of sodium hydroxide in 80 ml of ethanol. The reaction mixture is then heated up to 50° C. and allowed to react for 5 hours, whilst stirring, until a clear colourless solution forms. The solution is diluted with 550 ml of ethanol and cooled to −50° C. using solid carbon dioxide. 29 g of a crystalline methylol compound of the formula

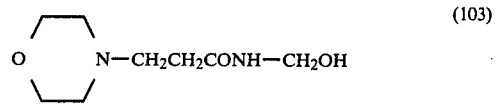

which has melting point of 92°–93° C. are obtained.

(b) 9.3 g of filter paper are so saturated with a 10% strength aqueous solution of the methylol compound of the formula (103) which has been adjusted to a pH of 3 that 33.3 g of the acid solution are taken up by the paper. The paper is dried for 10 minutes at 110° C. and then worked up as described in Instruction A. (b). The nitrogen content of this adsorbent material is 1.6%, 0.8% of which is basic nitrogen.

D.

(a) 68.5 g of an adduct (melting point: 236°–237°) obtained by an addition reaction of 2 mols of acrylamide with 1 mol of piperazine are dissolved in 313 ml of water and methylolated with 51.3 g of a 35.1% strength solution of formaldehyde, with the addition of 0.1 g of sodium hydroxide, for 5 hours at 50°–60° C. A clear solution which has a formaldehyde content of 0.09% forms. This solution is then completely evaporated and the residue is recrystallized from a mixture of ethanol and methanol (1:1).

27 g of a methylol compound of the formula

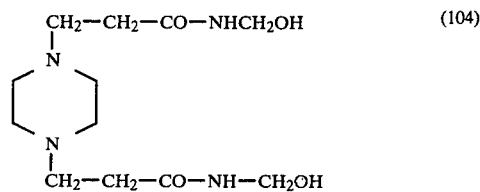

which has a melting point of 151°–153° C. are obtained.

(b) 9.6 g of filter paper are so saturated with a 10% strength aqueous solution of the methylol compound of the formula (104), which has been adjusted to a pH of 3 with concentrated hydrochloric acid, that 34.6 g of the acid solution are taken up by the paper. The treated paper is dried for 10 minutes at 110° C. and then worked up as described in Instruction A (b). The nitrogen content of the resulting adsorbent material is 2.52%, 1.26% of which is basic nitrogen.

E.

(a) 50 g of the product (melting point: 278°–282° C. with decomposition) obtained by reacting piperazine and chloracetamide are dissolved in 315 ml of water and methylolated with 42.8 g of a 35.1% strength solution of formaldehyde, with the addition of 0.1% of sodium hydroxide. The resulting solution, which contains the methylol compound of the formula

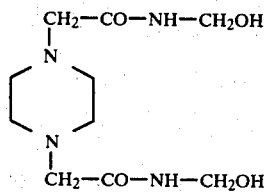 (105)

which has a formaldehyde content of 0.06%, is diluted with 242 ml of water and the pH value is adjusted to 3 with concentrated hydrochloric acid.

(b) 9.4 g of filter paper are so saturated with the acid solution, prepared according to (a), of the methylol compound of the formula (105) that 33.7 g of this solution are taken up by the paper. The impregnated paper is dried for 10 minutes at 120° C. and then worked up as described in Instruction A (b). The nitrogen content of the resulting adsorbent material is 2.5%, 1.25% of which is basic nitrogen.

F.

(a) 22.6 g of the morpholinium compound of the formula

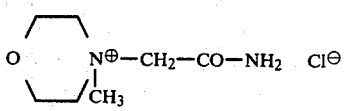

are dissolved in 110 ml of water and methylolated with 9.6 g of a 36.5% strength solution of formaldehyde, with the addition of 0.05 g of sodium hydroxide, for 5 hours at 50.55° C. to give a methylol compound of the formula

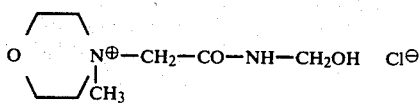 (106)

which has a formaldehyde content of 0.04%. The resulting solution is then diluted with 118 ml of water and the pH is adjusted to 3 with concentrated hydrochloric acid.

(b) 9.4 g of filter paper are so saturated with the acid solution, prepared according to (a), of the methylol compound of the formula (106) that 34.9 g of this solution are taken up by the paper. The impregnated paper is dried at 140° C. for 10 minutes and worked up as described in Instruction A. (b). The nitrogen content of the resulting adsorbent material is 0.8%, 0.4% of which is basic nitrogen.

G.

(a) 27.2 g of the adduct obtained by an addition reaction of 2 mols of acrylamide with 1 mol of N,N-diethylaminopropylamine are dissolved in 150 ml of ethanol and quaternised with 11 g of ethyl bromide for 5 hours at 60°–70° C. The resulting solution is then evaporated at 50° C., after which 35.9 g of the partially quaternised ammonium compound are obtained in the form of a viscous oil. The ammonium compound is dissolved in 185 ml of water and methylolated with 16.4 g of a 36.5% strength solution of formaldehyde, with the addition of 0.05 g of sodium hydroxide, for 5 hours at 50°–60° C. to give a methylol compound of the formula

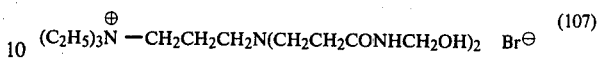 (107)

which has a formaldehyde content of 0.04%. The resulting solution of the methylol compound is diluted with 182 ml of water and the pH is adjusted to 3 with concentrated hydrochloric acid.

(b) 9.6 g of filter paper are so saturated with the acid solution prepared according to (a) that 36.2 g of this solution are taken up by the paper. The impregnated paper is dried for 10 minutes at 130° C. and worked up as described in Instruction A. (b). The nitrogen content of the resulting adsorbent material is 2%, 1.0% of which is basic nitrogen.

H.

(a) 22.5 g of a 36.9% strength solution of hydrochloric acid are added to a solution of 34.9 g of 2-dimethylaminopropionamide in 22.5 ml of water, whilst cooling. 30.4 g of a 35.1% strength solution of formaldehyde and 20 ml of water are then added at room temperature, whilst stirring. After a reaction time of 2 days at 25° C., the conversion of formaldehyde is 98% of theory. A 35% strength aqueous solution of a methylol compound of the formula

(CH$_3$)$_2$N—CH$_2$CH$_2$—CONH—CH$_2$OH  (108)

approximately 80% of which is in the form of the hydrochloride, is obtained.

The pH of 46 g of this solution is adjusted to 4 with 18% strength hydrochloric acid and the mixture is diluted with 30 ml of water.

(b) 7.7 g of filter paper are so saturated with the acid solution prepared according to (a) that 25.5 g of the acid solution are taken up by the paper. The impregnated paper is heat-set for 10 minutes at 140° C. and then worked up as described in Instruction A. (b). 8.3 g of an adsorbent are obtained. The nitrogen content of this adsorbent material is 2.0%, 1% of which is basic nitrogen.

I.

(a) 69.7 g of an addition product of bis-(2-ethoxyethyl)-amine and acrylamide are dissolved in 22.5 ml of water and 22.5 g of 36.5% strength hydrochloric acid are added, whilst cooling. 15 ml of water, 30.4 g of a 35.5% strength solution of formaldehyde, 15 ml of water and 30 ml of a 2 N sodium hydroxide solution are then added at 25° C., whilst stirring. After a reaction time of 14 days at 25° C., the conversion of formaldehyde is 96% of theory. 207 g of a 38% strength aqueous solution of the methylol compound of the formula

(C$_2$H$_5$OCH$_2$)$_2$N—CH$_2$CH$_2$—CONH—CH$_2$OH  (109)

approximately 80% of which is in the form of the hydrochloride, are obtained.

The pH of this solution is adjusted to 4 with dilute hydrochloric acid and the mixture is diluted with water to give a 20% strength solution.

(b) Using the acid solution prepared according to (a), filter paper is so saturated, and heat-set, as described in Instruction H. (b), that 8.3 g of an adsorbent are obtained. The nitrogen-content of this adsorbent material is 1.6%, 0.8% of which is basic nitrogen.

J.

(a) 144 g of 2-diethylaminopropionamide, 90 g of paraformaldehyde and 0.6 g of magnesium oxide are allowed to react for 40 minutes at 96°–98° C., whilst stirring, the conversion of formaldehyde being 100% of theory. The reaction product is then cooled to 40° C. and water is then added. 430 g of a 47% strength solution of the dimethylol compound of the formula

(C₂H₅)₂N—CH₂CH₂—CON(CH₂OH)₂ (110)

are obtained. The pH of 33.4 g of this solution is adjusted to 4 with 5 N hydrochloric acid and the solution is diluted with water to a weight of 80 g.

(b) Using the acid solution prepared according to (a), filter paper is so saturated, and heat-set, as described in Instruction H. (b), that 9.0 g of an adsorbent are obtained. The nitrogen content of this adsorbent material is 2.5%, 1.25% of which is basic nitrogen.

K.

(a) 144 g of 2-diethylaminopropionamide are dissolved in 300 ml of benzene and 31.2 g of paraformaldehyde and 0.2 g of sodium methylate are added. The mixture is allowed to react for 10 hours at 45° C., whilst stirring. 91.4 g of a 36.9% strength solution of hydrochloric acid and 92 g of methanol are then added at room temperature. The emulsion formed is slowly heated to the boil and the water is distilled off as an azeotrope. The residue is then evaporated, after which 198 g of a compound of the formula (C₂H₅)₂N—CH₂CH₂—CONH—CH₂OCH₃.HCl (111)

are obtained.

(b) Using a 20% strength aqueous solution of the compound prepared according to (a), filter paper is so saturated, and heat-set, as described in Instruction H. (b), that 8.7 g of an adsorbent are obtained. The nitrogen content of this adsorbent material is 2.6%, 1.3% of which is basic nitrogen.

L.

(a) 56 g of pyridine are added to a solution of 75.2 g of 2-chloropropionamide in 750 ml of dioxane at 50° C., whilst stirring. This mixture is stirred at a temperature of 100° C. for 18 hours. The precipitate which has formed on cooling is filtered off and recrystallised from ethanol. 65 g of a compound of the formula

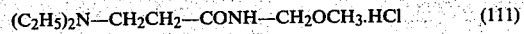

are obtained. 28.9 g of this compound are dissolved in 60 ml of water, 15.8 g of a 35.5% strength solution of formaldehyde are added and the mixture is stirred for 14 days at room temperature. The pH value of the reaction mixture is kept at 8 by adding a 1 N sodium hydroxide solution.

The conversion of formaldehyde is 67% of theory. 115 g of a 29% strength solution of the methylol compound of the formula

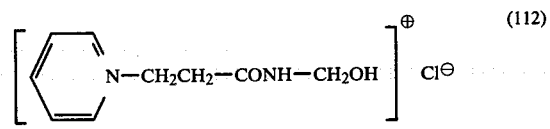

are obtained. The pH of this solution is adjusted to 4 with hydrochloric acid and the mixture is diluted with water to give a 10% strength solution.

(b) Using the acid solution prepared according to (a), filter paper so so saturated, and heat-set, as described in Instruction H. (b), that 9.0 g of an adsorbent are obtained. The nitrogen content of this adsorbent material is 1.9%, 0.95% of which is basic nitrogen.

M.

(a) 25 g of a 36% strength solution of formaldehyde are added to a solution of 45.7 g of carbamoylcholine chloride in 150 ml of water. This mixture is stirred at a temperature of 25° C. for 3 days and the pH value is kept at 8.5 by adding a 0.1 N sodium hydroxide solution. The conversion of formaldehyde is 95% of theory. A 24% strength solution of a methylol compound of the formula

[(CH₃)₃N—CH₂CH₂—O—CO—NH—CH₂OH]⊕· Cl⊖ (113)

is obtained. The pH of this solution is adjusted to 4 with hydrochloric acid and the mixture is diluted with water to give a 10% strength solution.

(b) 7.7 g of paper are so saturated with the acid solution prepared according to (a) that 23 g of the solution are taken up by the paper. The impregnated paper is dried for 5 minutes at 170° C. and then worked up as described in Instruction A. (b). The nitrogen content of the adsorbent material is 0.9%, 0.45% of which is basic nitrogen.

N.

(a) 20 g of a copolymer of the formula

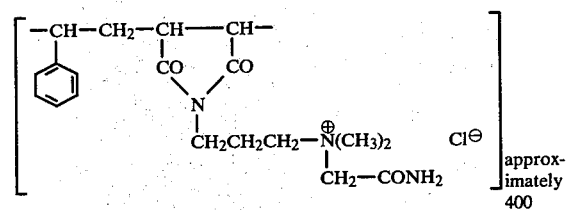

are dissolved in 80 g of water and 8.9 g of a 35.5% strength solution of formaldehyde are added. The reaction solution is then heated to 55° C. and the pH value is kept at between 8 and 8.5 by adding 1 N sodium hydroxide solution. After a reaction time of 17 hours, the conversion of formaldehyde reaches 96% of theory. 113 g of a 20% strength clear solution of the methylolated polymer of the formula

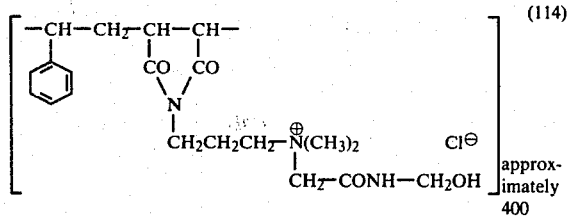

are obtained. The pH of this solution is then adjusted to 4 with concentrated hydrochloric acid and the mixture is diluted with water to give a 10% strength solution.

(b) Using the acid solution prepared according to (a), 7.7 g of filter paper are so saturated, and heat-set, as described in Instruction H. (b), that 10.7 g of an adsorbent are obtained. The nitrogen content of this adsorbent material is 2.1%, 0.7% of which is basic nitrogen.

O.

(a) 25.5 g of a polymer of the formula

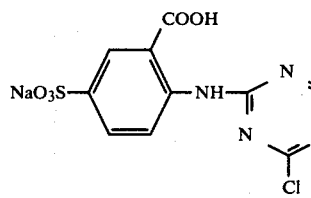

which has been obtained by a condensation reaction of diethyl adipate with 4-aza-4-methylheptamethylenediamine, are dissolved in 18 ml of dimethylformamide. 12.3 g of N-methoxymethyl-α-chloracetamide are added to this solution at 70° C., whilst stirring. The reaction mixture is stirred for a further 18 hours at 80°–85° C. and is finally evaporated. The residue is dissolved in 147 ml of water. A 20% strength solution of a polymer of the formula

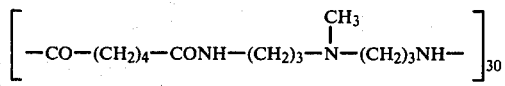

is obtained, the conversion of the chloride ion being 88% of theory.

The pH of this solution is then adjusted to 4 with concentrated hydrochloric acid and the mixture is diluted with water to give a 10% solution.

(b) Using the acid solution prepared according to (a), 7.7 g of filter paper are so saturated, and heat-set, as described in Instruction H. (b), that 8.4 g of an adsorbent are obtained. The nitrogen content of this adsorbent material is 1.8%, 0.45% of which is basic nitrogen.

P.

7.7 g of filter paper are so saturated with a solution which comprises 20 parts of the methylol compound of the formula (102), 4 parts of dimethylolmelamine and 76 parts of water/5 N hydrochloric acid and has been adjusted to a pH of 4 that 24.3 g of this solution are taken up by the paper. The impregnated paper is dried for 10 hours at 140° C. and then worked up as described in Instruction A. (b). 9.4 g of an adsorbent with a nitrogen content of 6% are obtained.

EXAMPLES 1 to 7

5 l of a red coloured residual liquor which still contains 20 mg/l of the dyestuff of the formula

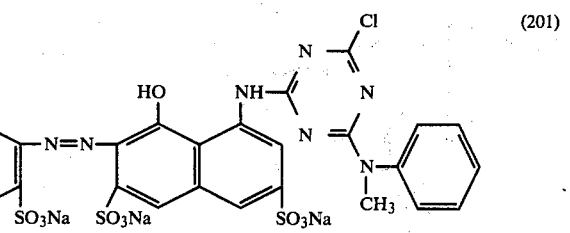

in a dissolved form and the pH value of which has been adjusted to 5.5 are initially introduced into a stirred reactor. The dye liquor is heated to a temperature of 50° C. and in each case 1 g of one of the cationically modified cellulose materials which have been prepared according to Instructions A to G and which have previously been suspended in 100 ml of water is added. In each experiment, a sample is taken after an adsorption time of 10 minutes and 30 minutes and the samples are filtered through a fluted filter and the concentration of dyestuff in the filtrate which is indicated in Table 1 is determined.

TABLE 1

| Example No. | Adsorbent prepared according to Instructions | Residual dyestuff concentration in mg/l | |
|---|---|---|---|
| | | after 10 minutes | 30 minutes |
| 1 | A. (b) | 1.8 | 0.06 |
| 2 | B. (b) | 0 | 0 |
| 3 | C. (b) | 1.2 | 0 |
| 4 | D. (b) | 0.6 | 0 |
| 5 | E. (b) | 0.7 | 0 |
| 6 | F. (b) | 7 | 4.8 |
| 7 | G. (b) | 0.4 | 0 |

Similarly good decolorising effects are obtained in the fixed bed process when the adsorbents indicated in Examples 1 to 7 are used in the form of chips.

EXAMPLE 8

If a residual liquor which has a pH value which has been adjusted to 8 is used in Example 7 and in other respects the procedure is as indicated for Example 7, samples which are taken after an adsorption time of 10 minutes and of 30 minutes display, respectively, a dyestuff concentration of only 0.7 mg/l and complete decoloration.

If, in Examples 1 to 8, a residual liquor which contains one of the following dyestuffs of the formulae (202) to (209) in place of the dyestuff of the formula (201) indicated in the said examples is employed, the samples taken after an adsorption time of 10 minutes and of 30 minutes display virtually complete decloration.
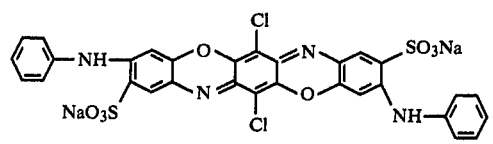 (202)
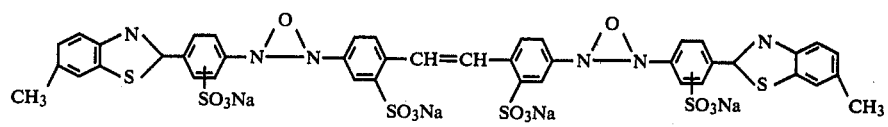 (203)
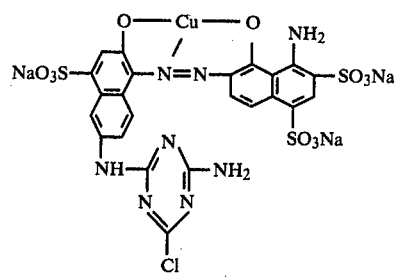 (204)
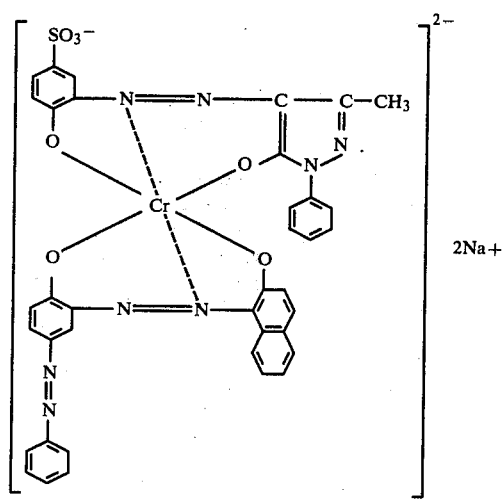 (205)
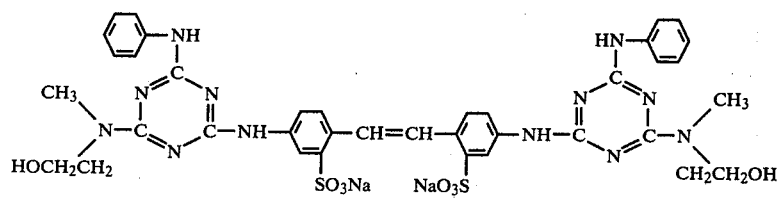 (206)
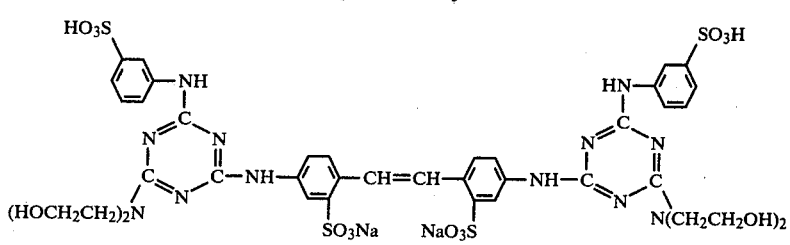 (207)
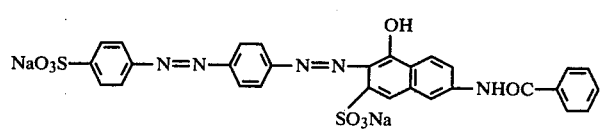 (208)

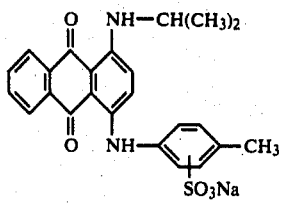

EXAMPLE 9

50 l of a violet coloured waste print-rinsing liquor which is at 48° C. and has a TOC content of 39 mg/l are brought into contact, in the manner described in Examples 1 to 8, with 60 g of the adsorbent prepared according to Instructions A. (b) to G. (b). After a treatment time of 10 minutes, a sample filtrate is, in each case, completely colourless and has a TOC content of only 8 mg/l. (TOC=total organic carbon).

EXAMPLES 10 to 18

5 l of a red coloured residual liquor which still contains 100 mg/l of the dyestuff of the formula (201) in a dissolved form and the pH value of which has been adjusted to 7 are initially introduced into a stirred reactor. The dye liquor is heated to a temperature of 50° C. and in each case 0.5 g of one of the cationically modified cellulose materials which have been prepared according to Instructions H to P and which have previously been suspended in 50 ml of water is added. In each experiment, a sample is taken after an adsorption time of 30 minutes and is filtered through a fluted filter and the capacities indicated in Table 2 are determined for the adsorbents employed.

TABLE 2

| Example No. | Adsorbent prepared according to Instructions | Capacity* |
|---|---|---|
| 10 | H. (b) | 11 |
| 11 | I. (b) | 12 |
| 12 | J. (b) | 27 |
| 13 | K. (b) | 31 |
| 14 | L. (b) | 24 |
| 15 | M. (b) | 12 |
| 16 | N. (b) | 12 |
| 17 | O. (b) | 10 |
| 18 | P. | 30 |

*Capacity = $\frac{\text{amount of adsorbed dyestuff} \cdot 100}{\text{amount of adsorbent}}$

We claim:

1. A basic methylolamide compound of the formula

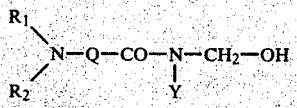

or a salt thereof, in which $R_1$ and $R_2$ independently of one another denote hydrogen, lower alkyl which is unsubstituted or substituted by halogen, hydroxyl, lower alkoxy or cyano, or cycloalkyl, benzyl or the group of the formula

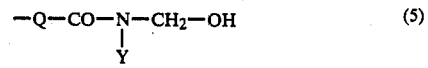

Q denotes an alkylene- or alkyl-substituted alkylene chain with 2 to 8 carbon atoms and Y denotes hydrogen, lower alkyl or —CH$_2$OH.

2. A basic N-methylolamide compound of claim 1 of the formula

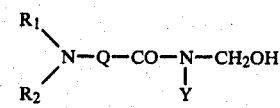

or a salt thereof, wherein each of $R_1$ and $R_2$ represents lower alkyl or lower alkoxy-lower alkyl Q is $C_2$–$C_3$-alkylene and Y represents hydrogen, lower alkyl or —CH$_2$OH.

3. A compound according to claim 2, wherein $R_1$ and $R_2$ are lower alkyl.

4. A compound according to claim 2, wherein Y is hydrogen.

5. A N-methylolamide compound according to claim 2 of the formula

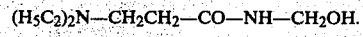

6. A N-methylolamide compound according to claim 2 of the formula

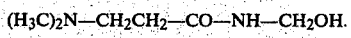

7. A N-methylolamide compound according to claim 2 of the formula

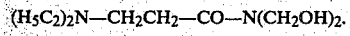

8. A N-methylolamide compound according to claim 2 of the formula

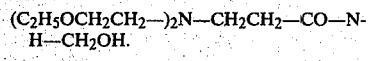

* * * * *

UNITED STATES PATENT AND TRADEMARK OFFICE
CERTIFICATE OF CORRECTION

PATENT NO. : 4,306,080
DATED : December 15, 1981
INVENTOR(S) : Jaroslav Hasse et al It is certified that error appears in the above—identified patent and that said Letters Patent is hereby corrected as shown below:

Title page, Assignee line delete "Ciba-Geigy Corporation, Basel, Switzerland
and substitute --Ciba-Geigy Coproation, Ardsley, New York, New York --.

Signed and Sealed this

First Day of June 1982

[SEAL]

Attest:

GERALD J. MOSSINGHOFF

*Attesting Officer*    *Commissioner of Patents and Trademarks*